United States Patent

Joshi et al.

[11] Patent Number: 5,951,538
[45] Date of Patent: Sep. 14, 1999

[54] GAS GENERATING DEVICE FOR DELIVERING BENEFICIAL AGENTS TO A BODY CAVITY

[75] Inventors: Ashok V. Joshi, Salt Lake City; Giorgio di Palma, Draper; Truman Wold, Salt Lake City, all of Utah

[73] Assignee: Ceramatec, Inc., Salt Lake City, Utah

[21] Appl. No.: 08/908,687

[22] Filed: Aug. 7, 1997

[51] Int. Cl.[6] .................................................. A61M 31/00
[52] U.S. Cl. .......................... 604/500; 604/502; 604/514
[58] Field of Search .............................. 604/890.1, 891.1, 604/73, 93, 131, 140–141, 143, 145, 257, 262, 403, 408, 410; 128/DIG. 24; 222/92, 206

[56] References Cited

U.S. PATENT DOCUMENTS

| | | |
|---|---|---|
| 3,840,009 | 10/1974 | Michaels et al. . |
| 4,312,347 | 1/1982 | Magoon et al. . |
| 4,326,522 | 4/1982 | Guerrero et al. . |
| 4,425,117 | 1/1984 | Hugemann et al. . |
| 4,439,197 | 3/1984 | Honda et al. . |
| 4,457,752 | 7/1984 | Vadasz . |
| 4,564,363 | 1/1986 | Bagnall et al. . |
| 4,892,778 | 1/1990 | Theeuwes et al. ...................... 604/145 |
| 4,969,873 | 11/1990 | Steinbach et al. ...................... 604/145 |
| 5,135,523 | 8/1992 | Margruder et al. . |
| 5,162,116 | 11/1992 | Shepherd . |
| 5,196,002 | 3/1993 | Hannover et al. . |
| 5,431,919 | 7/1995 | Maruyama et al. . |
| 5,553,741 | 9/1996 | Sancoff et al. .......................... 604/145 |
| 5,700,245 | 12/1997 | Sancoff et al. .......................... 604/145 |
| 5,785,688 | 7/1998 | Joshi et al. .............................. 604/145 |

Primary Examiner—Wynn Wood Coggins
Assistant Examiner—Jennifer R. Sadula
Attorney, Agent, or Firm—Factor and Shaftal

[57] ABSTRACT

A controlled delivery device for holding and administering a biologically active agent includes a housing having a first end portion, a second end portion, and a port associated with the housing. Enclosed within the housing is a displacing member, a chemical or electrochemical gas generating cell, activation and control circuitry. The electrochemical or chemical cell generates gas within the housing, forcing the displacing member against the beneficial agents contained within the housing and forcing the beneficial agents through an outlet port and into an animal's body cavity at a predetermined rate. An anchoring mechanism may be associated with the housing for securing the housing inside the body cavity of the animal being treated. Also disclosed are methods of delivering the beneficial agents into the animal's body cavity using the delivery device of the present invention.

15 Claims, 5 Drawing Sheets

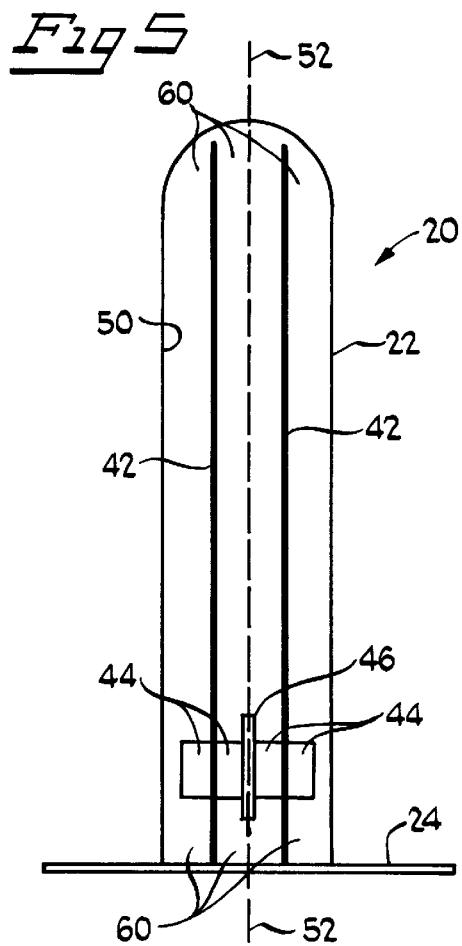
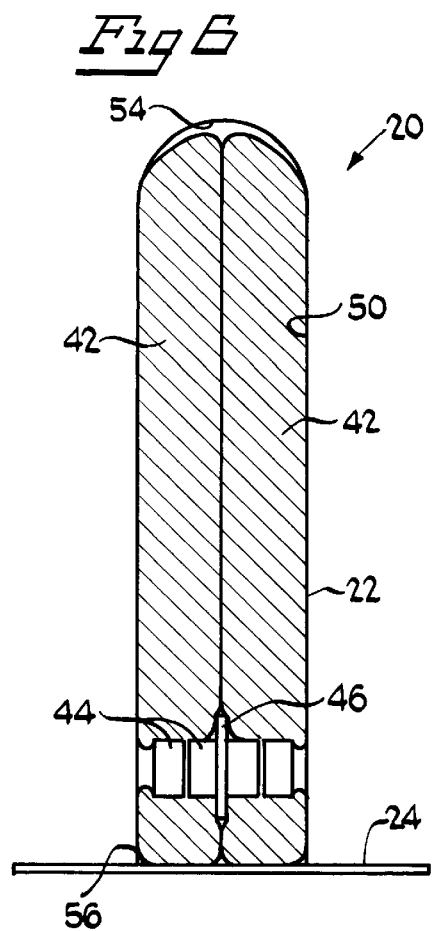
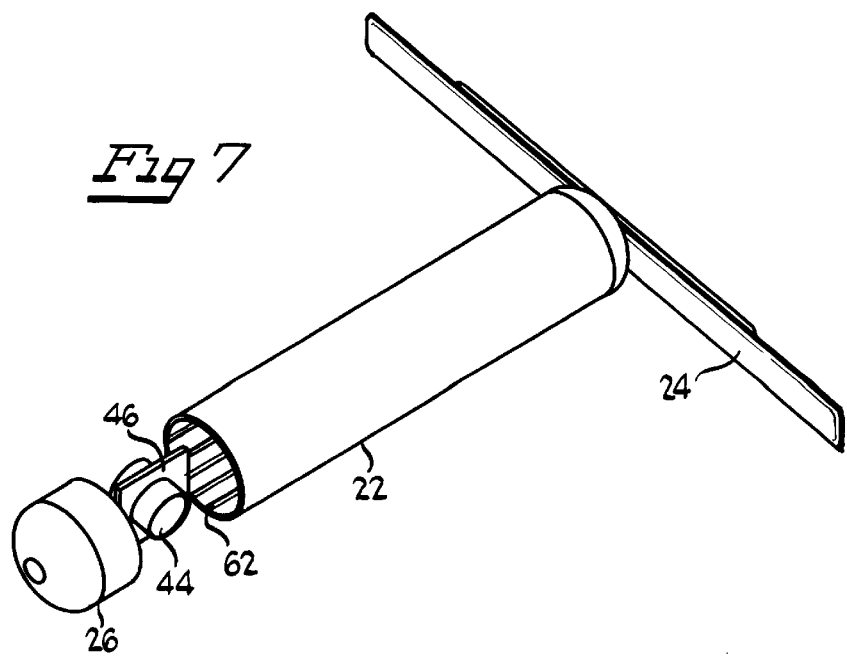

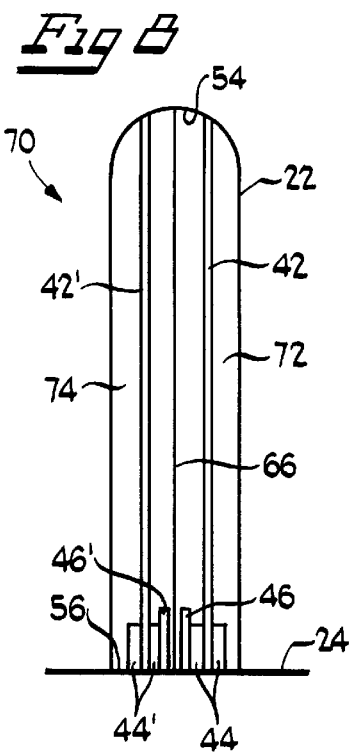
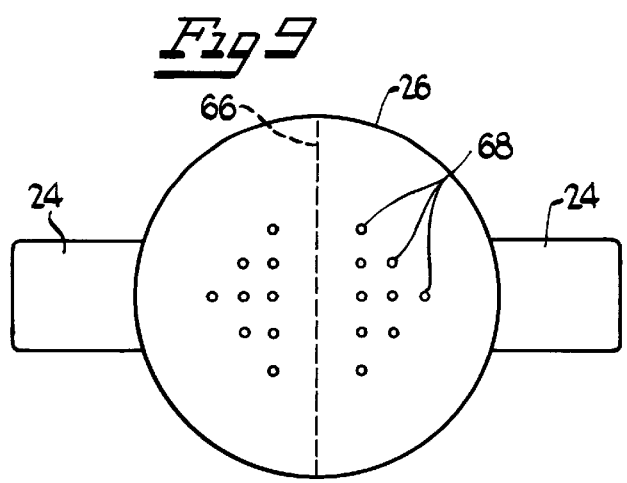
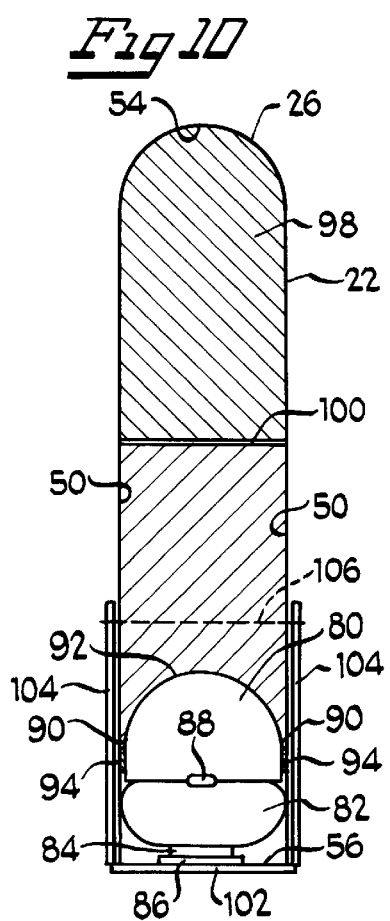
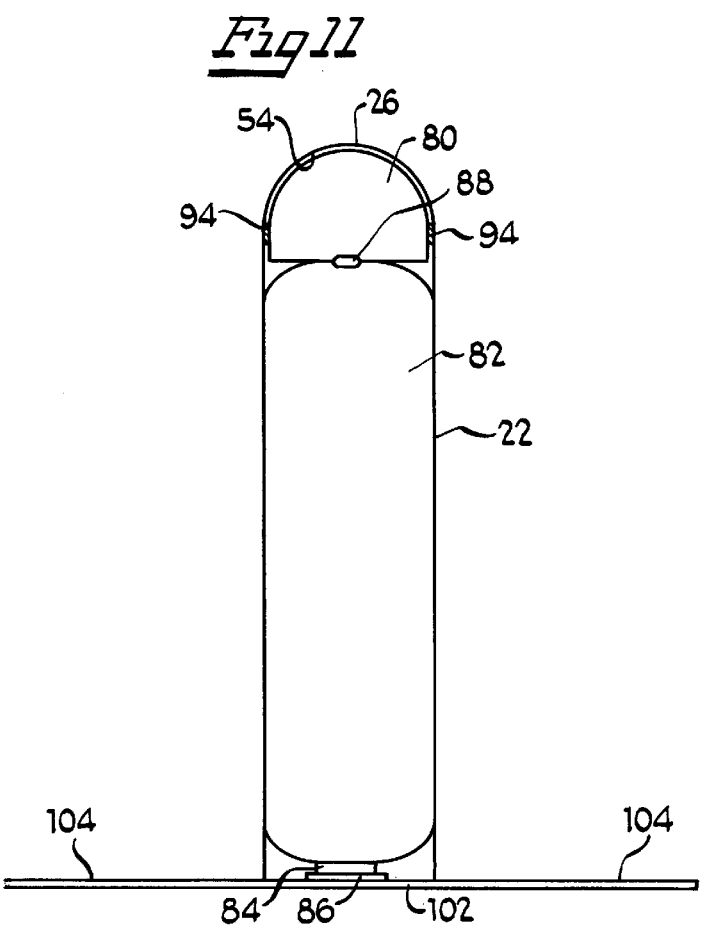

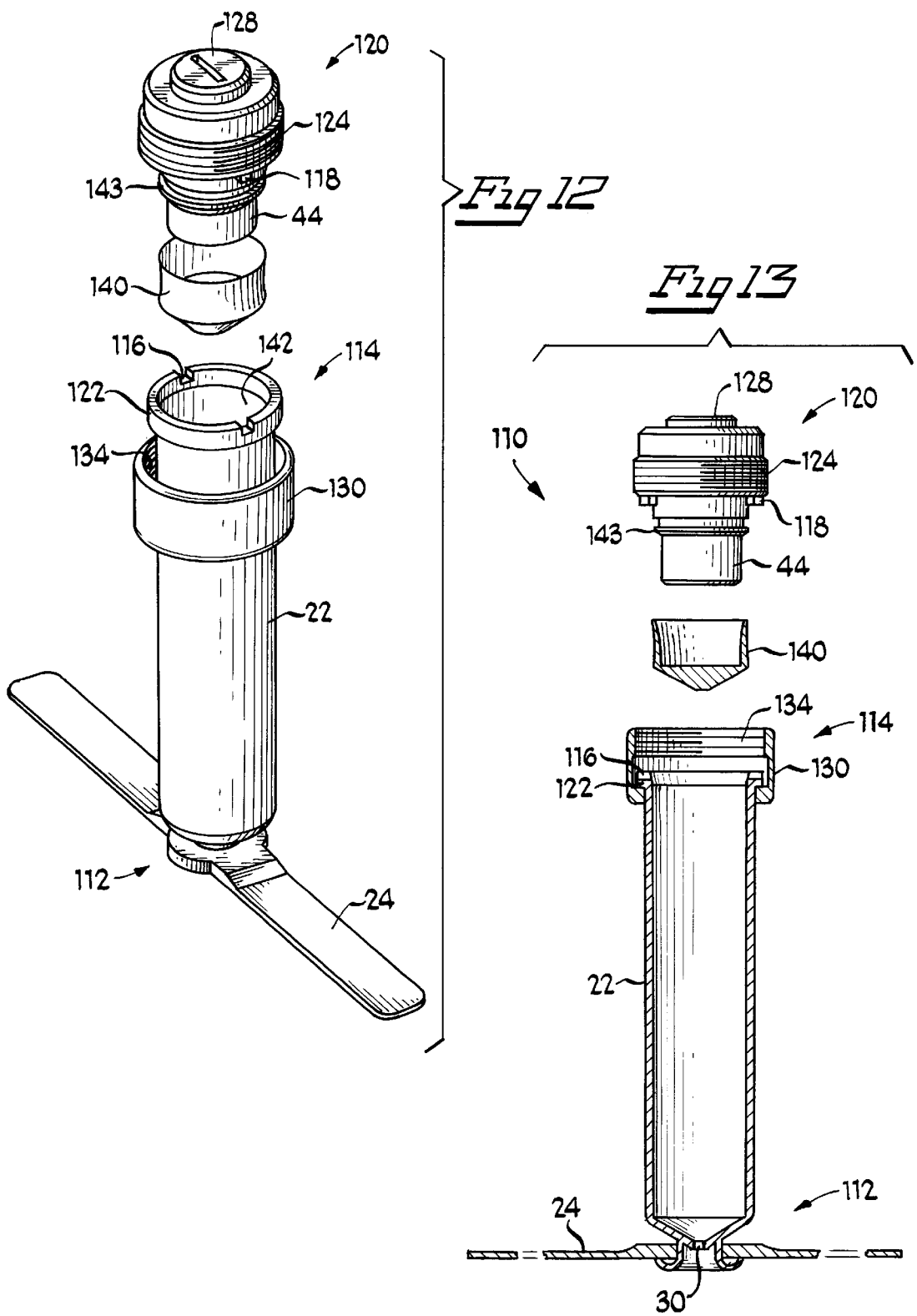

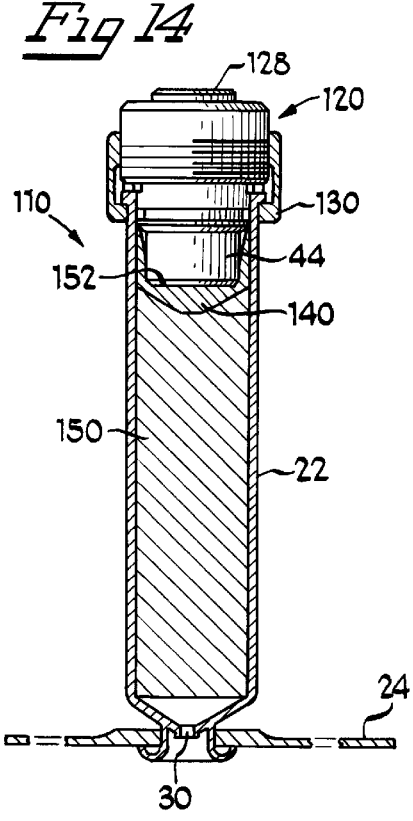
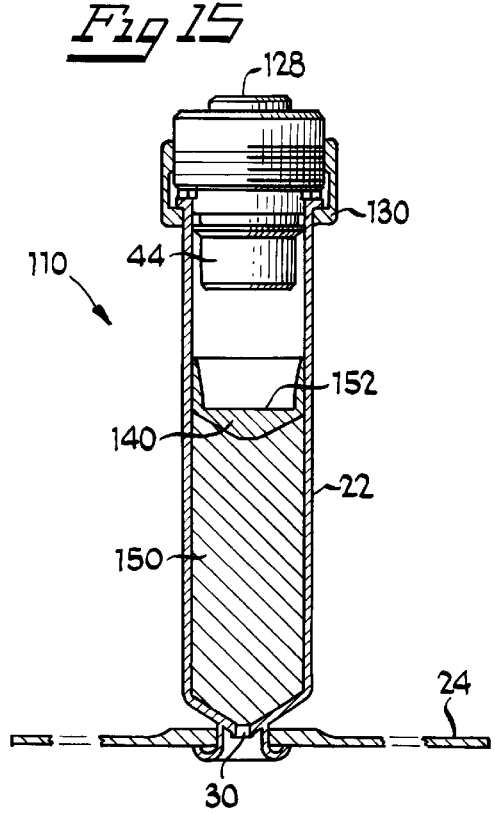
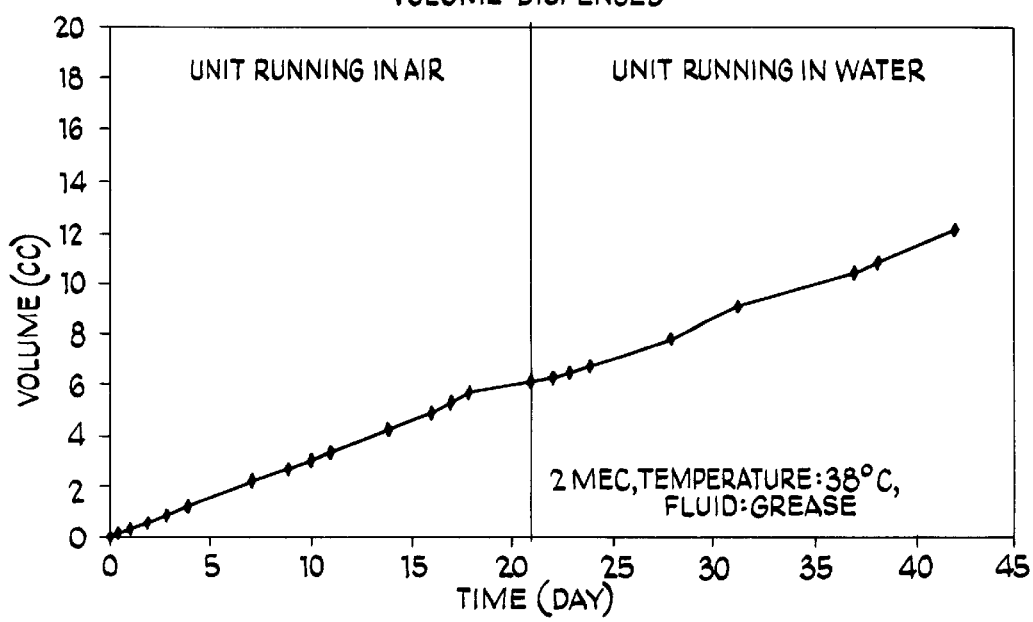

GAS GENERATING DEVICE FOR DELIVERING BENEFICIAL AGENTS TO A BODY CAVITY

TECHNICAL FIELD

The invention relates generally to a delivery system for administering a variety of beneficial agents to animals. More particularly, the invention relates to a dispenser or delivery device including a housing containing a biologically active agent and an electrochemical and/or chemical gas generating cell to move a displacing member within the housing. Movement of the displacing member displaces a biologically active agent out of the container, preferably into the ruminal cavity or stomach of an animal.

BACKGROUND

In the fields of veterinary medicine and animal husbandry it is sometimes desirable to treat animals via periodic administration of various drugs and agents. Where the course of therapy requires multiple or repetitive administration of drugs or agents, the animals must be located, captured, and restrained until the drug or agent is administered. This process is repeated for each subsequent dosage or administration, which can consume a great deal of time and resources, while potentially endangering the animals and the veterinarian or farm worker. In an effort to alleviate this problem, a number of delivery systems for administering beneficial agents to animals have been disclosed. Examples of such devices are disclosed in U.S. Pat. No. 5,196,002 (Mar. 23, 1993) to Hanover et al.; U.S. Pat. No. 5,162,116 (Nov. 10, 1992) to Shepherd; U.S. Pat. No. 4,564,363 (Jan. 14, 1986) to Bagnall et al.; U.S. Pat. No. 4,457,752 (Jul. 3, 1984) to Vadasz; U.S. Pat. No. 4,439,197 (Mar. 27, 1984) to Honda et al.; and U.S. Pat. No. 4,425,117 (Jan. 10, 1984) to Hugemann et al.

While such devices deliver an agent to the body of an animal in which they are placed, the devices collectively possess a number of disadvantageous limitations. For example, the devices generally lack specific controlled release capabilities, are limited to specific applications, are limited to continuous delivery of the contents therein, are large and difficult to place and maintain in specific areas of the body, or are relatively complicated and costly to manufacture and use. Additionally, many of the existing devices are made of or contain parts that are made of metal (e.g., springs within the housing) which can damage tools, such as a saw blade, or the worker during the dissection or slaughter of the animal. Other devices, such as the osmotic device disclosed in U.S. Pat. No. 5,431,919 (Jul. 11, 1995) to Maruyama et al. also possess shortcomings since they depend on the surrounding water found in ruminal fluid of a ruminant to deliver its contents and does not provide delivery at a constant rate.

Therefore, it would be advantageous to provide a compact, easily manufactured, simple and efficient delivery device which may be introduced into the body of an animal for timed, periodic, controlled and/or slow release of drugs or agents into the animal. It would also be advantageous to provide a delivery device which is reliable, contains a high ratio of contents (i.e., drugs or beneficial agents) in relation to the volume of the container or package, and is made of materials that are lightweight and easy to cut. It would be also advantageous to provide a device which is made up of biologically as well as environmentally friendly materials.

DISCLOSURE OF THE INVENTION

According to the present invention, a delivery device includes a housing, having a first end and a second end, for holding a biologically active agent and discharging the same through an outlet port associated with the housing. Enclosed within the housing is a displacing member fluidically associated with an electrochemical or chemical gas generating cell, which may be controlled either by an electrical circuit, or by chemical reaction via activation to produce a gas at a constant or predetermined rate. Generation of the gas moves the displacing member, which, in turn, pushes the beneficial agents out of the housing through the outlet port. An anchoring mechanism is associated with the housing for securing and maintaining the housing inside a body cavity of the animal being treated.

In a preferred embodiment, the invention includes a movable plunger or piston enclosed within the housing which forms a sealed chamber that is in fluid association with the electrochemical or chemical gas generating cell. Generation of the gas pushes the plunger toward the outlet port to force the beneficial agents out of the housing and into a body cavity, such as the stomach or rumen of the animal.

Another preferred embodiment includes a bag in fluid association with the electrochemical or chemical gas generating cell. Generation of the gas inflates the bag, which in turn displaces and pushes the beneficial agents out of the housing through the outlet port.

The invention also includes a multi-chambered delivery device having a plurality of bags and/or electrochemical gas generating cells for delivering a plurality of beneficial agents out of the housing through an outlet port.

The invention may also include a delivery device having a plunger or piston and a bag associated with the plunger is disclosed. The bag is fluidically associated with an electrochemical or chemical gas generating cell that generates gas for delivery to the interior of the bag and inflates the bag. Inflation of the bag pushes the plunger toward an outlet port, thus pushing beneficial agents located between the plunger and port out of the housing and into the stomach or rumen of the animal being treated.

The invention also includes methods of delivering beneficial agents into an animal's body cavity.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

FIGS. 5 and 6 are cross-sectional views of the delivery device of FIG. 1 in pre-delivery and post-delivery phases, respectively;

FIG. 7 is an exploded view of the delivery device, showing the positioning of an electrical circuit and gas generating cell in relation to the housing;

FIG. 8 is a cross-sectional view of a second embodiment of a delivery device made in accordance with the present invention;

FIG. 9 is a top view of the delivery device of FIG. 8;

FIGS. 10 and 11 are cross-sectional views of a third embodiment of the delivery device made in accordance with the principles of the invention, showing the delivery device in its pre-delivery and post-delivery phases, respectively;

FIG. 12 is an exploded assembly view of a fourth embodiment of the delivery device made in accordance with the principles of the invention;

FIG. 13 is an exploded cross-sectional view of the delivery device of FIG. 12; and FIGS. 14 and 15 are cross-sectional views of the delivery device shown in FIGS. 12 and 13, showing the delivery device at various stages of the delivery phase; and FIG. 16 is a chart illustrating the performance characteristics of the delivery devices of FIGS. 14 and 15 during use.

BEST MODE OF THE INVENTION

Figure 1:
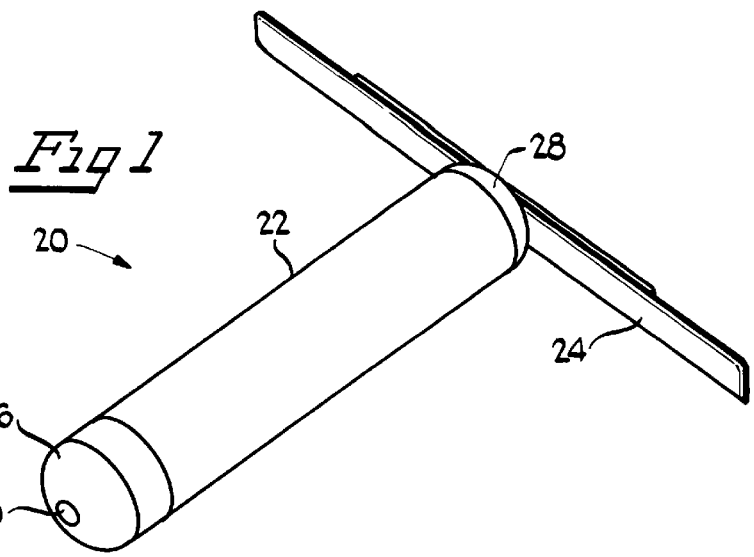
FIG. 1 is a perspective view of a first embodiment of a delivery device made in accordance with the invention.
Figure 2:
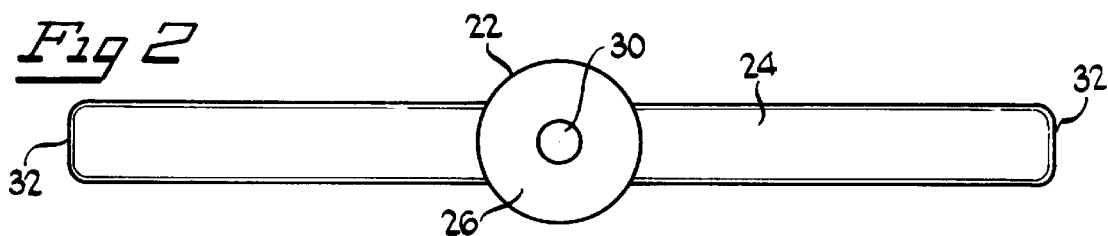
FIG. 2 is a top view of the delivery device of the preceding figure.
Figure 3:
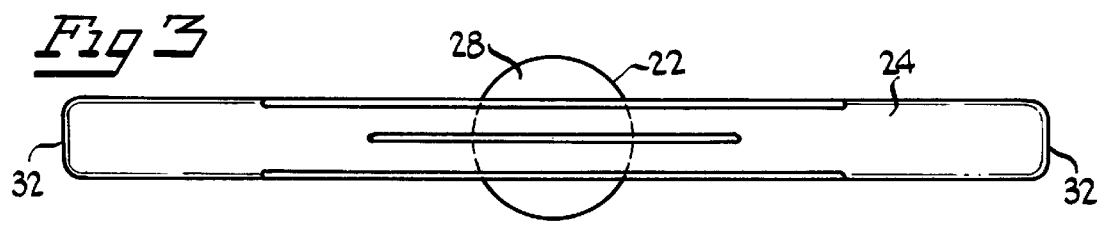
FIG. 3 is a bottom view of the delivery device of the preceding two figures.

Referring to FIGS. 1 through 3 of the drawings, there is shown a delivery device generally 20 made in accordance with the present invention which includes a housing 22, having a first end 26 and a second end 28, and an anchoring mechanism 24 attached to the second end 28. The first end 26 and second end 28 can be removably attached (e.g. by interacting threads) to the central portion of housing 22 to facilitate assembly of the hereinafter described internal mechanisms into the housing 22. After final assembly, first end 26 and second end 28 may be permanently bonded or secured to the central portion or body of the housing 22. The housing 22 can be made of any suitable material known in the art, such as plastics (e.g. molded polyethylene terephthalates (PET) or metallized plastics), or any other suitable materials which exhibit extremely low permeability to gases such as hydrogen, oxygen, and carbon dioxide. These materials should also be easily cut and non-damaging to cutting instruments, such as a cutting blade. Although a variety of sizes and shapes are contemplated, the housing 22 is preferably sized to accommodate from about 10 cc to about 250 cc of beneficial agent.

As more thoroughly described herein, in the depicted embodiment, the first end 26 includes an outlet port 30 for release of the contents within the housing 22. Alternatively, outlet port 30 may be located in second end 28 or in the housing body (not shown). The outlet port 30 may be associated with a breakable cover or soluble membrane or a one-way valve (not shown) to facilitate the release of the contents (especially where thin fluids are involved) in the housing 22 without contaminating the unused portion found within the housing 22. Although the outlet port 30 is shown here as a single, round aperture (see FIG. 2), it is understood that a variety of different shapes, configurations, and number of outlet port(s) can be used. Additionally, outlet port(s) 30 are not limited to first end 26 and second end 28 placement and can be placed anywhere on the housing 22 so as to permit delivery of the contents in a number of directions and to a variety of locations within a body cavity. The characteristics, layout, and number of outlet port(s) 30 are dependent on the viscosity of the agent contained within the housing 22. Thus, the outlet port should have a shape and size that permits easy dispensation of the contents out of the delivery device 20.

As shown in FIGS. 1 through 3, the anchoring mechanism 24 is attached to second end 28, but may also be attached to first end 26. Likewise, the delivery device 20 can include a plurality of anchoring mechanisms. The outlet port 30 can be located either at an opposite end from that end to which the anchoring mechanism 24 is attached or can be made to perforate through the center of the anchoring mechanism 24.

The anchoring mechanism 24 is preferably made from of flexible material, such as plastic, to allow for the anchoring mechanism 24 to be bent or collapsed onto and in substantially parallel alignment with outer surfaces of the housing 22 (see illustration of collapsed device in FIG. 9). Those skilled in the art will recognize that a variety of other anchoring mechanism shapes and mechanisms are possible.

Alternatively, the anchoring mechanism 24 can be made of substantially rigid materials. Where rigid materials are used, the anchoring mechanism 24 preferably also includes a hinge mechanism to permit placement of the distal portions 32 of the anchoring mechanism 24 onto and in substantially parallel alignment with the outer surfaces of the housing 22. Additionally, a spring activation mechanism can be associated with the hinge mechanism to automatically extend the distal portions of the anchoring means 24 away from the housing 22 once the delivery device reaches an area of sufficiently large volume, such as a stomach. After such extension, the anchoring mechanism 24 will lie in a substantially perpendicular alignment in relation to the housing 22, as shown in FIGS. 1 through 3. It is understood that any other means known in the art for creating extension of the anchoring mechanism 24 to cause immobilization of the delivery device 20 within a body cavity can be utilized in the instant invention. For example, the anchoring mechanism 24 can also include a catch (not shown) to hold the extended anchoring mechanism 24 in place.

The various embodiments of the delivery device of the present invention are made by providing an electrochemical or chemical cell for generating gas and a displacing member that is sealingly associated and in fluid communication with the electrochemical or chemical cell. The electrochemical or chemical cell and displacing member are positioned within an enclosure which defines a volume for retaining the beneficial agent. The enclosure generally comprises a first portion and a second portion, each of which is sized and shaped to integrate with the other. The displacing member is then placed within the volume in the enclosure and the first portion and second portion of the enclosure are interconnected. As further detailed below, the displacing member can comprise either a fluid-tight bag or a piston.

Figure 4:
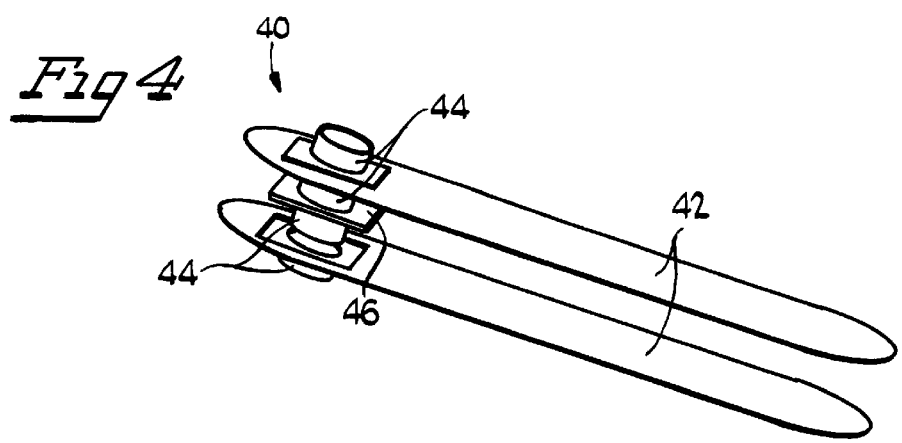
FIG. 4 is a perspective view of the bag assembly made in accordance with the principles of the invention.

Referring to FIG. 4, a bag assembly 40 is depicted which includes a bag or bladder 42, an electrochemical gas generating cell 44 sealingly attached to (or otherwise fluidically associated with) the bag 42, and an activation mechanism 46, such as an electrical circuit, attached to the electrical gas generating cell 44 in connection with the bag 42. In an alternative embodiment (not shown), the electrochemical cell is fluidically associated with the bag by means of a tube or conduit. The bag 42 can be made of any suitable material which is flexible and substantially impervious to fluids, gases, and chemicals. Although the depicted embodiment of the bag assembly 40 includes a specific number of components, any number of bag(s) 42, activation mechanism(s) 46, and/or electrochemical gas generating cell(s) 44 can be used in place of the illustrated embodiment to practice the present invention. For example, as shown in FIG. 5, the bag assembly 40 can include two bags 42 associated with a single electrochemical gas generating cell 44, which is attached to the activation mechanism 46.

The electrochemical or chemical gas generating cells 44 are capable of generating gases such as oxygen ($O_2$), hydrogen, nitrogen, halogen (e.g. $Cl_2$, bromine, iodine), carbon dioxide, and mixtures thereof, all of which are known. See, e.g., U.S. Pat. Nos. 4,402,817 and 4,522,698 to Maget (Jun. 11, 1985) which describe electrochemical cells. Preferred electrochemical cells for use with the invention include metal electrolyte electrochemical cells capable of generating hydrogen, oxygen, or mixtures thereof. Electrochemical cells include solid polymer electrolyte-based oxygen or hydrogen generators, zinc-electrolyte type hydrogen gas generating cells which use mercury (see, e.g., U.S. Pat. No. 5,245,565 to Winsel (Sep. 7, 1993) or U.S. Pat. No. 4,023,648 to Orlitzky et al.), $Cu(OH)_2$ or carbonate-based oxygen generating cells, NaSiCON-based $CO_2/O_2$ generating cells (see, International Application No. PCT/US96/04359 (International Publication No. WO 96/30563, published Oct. 3, 1996) to Ceramatec, Inc. (corresponding to co-owned, co-pending U.S. patent application Ser. No. 08/413,635 filed on Mar. 30, 1995, or nitrogen generating batteries (see, e.g., U.S. Pat. No. 5,427,870 (Jun. 27, 1995)). The contents of all of these referenced patents and patent application are incorporated by this reference. Preferred chemical cells for use with this invention include metal/electrolyte or bicarbonate/citric acid or peroxide/water cells which generate $H_2$, $CO_2$, oxygen respectively. Some cells require separate power sources (e.g. a battery), while others are self-powered.

As described in U.S. Pat. No. 4,902,278, a voltage gradient established across the electrochemical cell ionizes an electrochemically active material (e.g. atmospheric oxygen) at an electrode, transporting the ions through an electrolytic membrane to the other electrode, and reconverts the ions to molecules of the electrochemically active material which is evolved at the second electrode. In a presently preferred embodiment, a resistor is placed between the cells' electrodes (not shown) to activate the electrochemical cell while a mechanical action mechanism is placed to activate the chemical cell.

The activation mechanism 46 can operate in response to a variety of internally or externally generated signals. For example, the activation mechanism 46 can operate in response to a remotely transmitted signal (e.g. a radio transmission) received by a receiver and an antenna (neither shown) to selectively activate the gas generating cells 44. Alternatively, the activation mechanism 46 could incorporate internal timing circuitry to initiate activation of the gas generating cells 44 by the activation mechanism 46 at some predetermined time in the future (measured, for example, from the time that the delivery device is ingested by the animal) and/or at predetermined intervals. Remotely transmitted signals could also be used to initiate operation of the timing circuitry of the activation mechanism 46 so as to externally control the timing sequence at a selected moment. This method can be used in a variety of dosing regimens such as an intermittent dispensation cycle (e.g., every 8 hours or once a week), an extended time dosing cycle (e.g., continuous dosing over one hour), or in the administration of bolus dosages. Preferably, the method and apparatus of the invention will dispense the beneficial agent over a period of between 1 to 350 days.

In FIG. 5 is shown a second embodiment of the present invention wherein the bag assembly includes two bags 42, two gas generating cells 44, and the activation mechanism 46. For purposes of simplicity, structures and elements shared in common between the delivery device of FIG. 1 and various embodiments of the present invention will be numbered identically. Specifically depicted is the position of the bag assembly 40 in relation to the housing 22 of delivery device 20. The bag assembly 40 is placed within the housing 22, with the bags 42 being in substantially parallel alignment in relation to the internal surface 50 of housing 22. The gas generating cells 44 and the activation mechanism 46 can be located anywhere along the axis 52 of delivery device 20 and are only limited by the selected position of the outlet port(s) 30, which, as previously described, can be located anywhere on housing 22, first end 26, or second end 28. The remaining area 60 within the housing 22 contains a drug, beneficial agent, or combination thereof, for administration to the animal. These drugs and agents can be provided in any suitable dosage form (e.g. liquid, powder, paste, gel, grease stick, etc.). Likewise, a wide variety of agents and drugs can be administered through the invention. For example, hormones, enzymes, antibiotics, antifungals, and vitamins can be administered in a variety of dosage forms.

The bags 42 are provided for holding a gas or a mixture of gases. Inflation of the bags 42 occurs when the activation circuit 46 activates the gas generating cells 44. As shown in FIG. 6, the gas generating cells 44, upon activation, produce a gas (or gases) which fill the interior area of the bags 42, thus inflating the bags 42. Each bag 42 eventually inflates until contact is made with other bags 42, the interior surface 50 of the housing 22, interior surface 54 of first end 26, and interior surface 56 of second end 28. Thus, inflated bags 42 displace the contents that were previously found in area 60 (see FIG. 5) within housing 22. In this manner, the contents are pushed out of the housing 22 and introduced into an animal's body cavity (e.g. stomach, rumen, or rectal cavity). By controlling the activation of the gas generating cells 44, the rate and extent of inflation of the bags 42 can be manipulated to provide administration of agents over time, intermittently, as a single dosage unit, or as multiple and repetitive dosages, depending on the desired administration schedule and/or duration of therapy. Utilization of two bags 42 allows for administration of beneficial agents at different rates. For example, by activating the gas generating cells 44 to fill each of the bags 42 at different rates, the beneficial agent accordingly is displaced and forced out of the housing 22 in two specific administration rates. That is, a first bag can run at a fast, initial rate and then a second bag can expand at a slower rate to complete delivery of the beneficial agent.

FIG. 7 is a perspective, exploded view of the delivery device 20 exclusive of the bags 42, showing the positioning of the activation mechanism 46 and gas generating cells 44 in relation to the housing 22. Also shown are microgrooves 62 disposed on an inside surface of the housing 22. The microgrooves 62 are positioned to permit complete dispensing of the biologically active agent contained within the housing 22 even when the bags 42 are fully inflated and expand against the inside surface of the housing 22.

Once seen, those of skill in the art will be able to make and assemble the invention by inserting a bag assembly 40 into the volume within a housing 22 and interconnecting the first end 26 and second end 28 to the distal ends of the housing 22.

FIG. 8 shows a cross-sectional view of a second embodiment of the invention. For purposes of simplicity, structures and elements shared in common between the delivery device of FIGS. 1 through 7 and other embodiments of the present invention are numbered identically. A dual-chambered delivery device 70 includes a chamber wall 66 that separates chamber 72 (containing bag 42) from chamber 74 (containing bag 42'). The chamber wall 66 is attached to and extends between interior surface 54 of first end 26 and interior surface 56 of second end 28. The chamber wall 66 can be made of any suitable material known in the art, such as plastics (e.g. molded PET), metallized plastics, or any other suitable material which exhibits extremely low permeability to gases, such as hydrogen, oxygen, and carbon dioxide.

Gas generating cells 44 and 44' are attached to and in communication with bags 42 and 42', respectively. Bags 42 and 42' are each attached to and controlled by electronic circuitry 46 and 46', respectively. It is understood that the multi-chambered delivery device 70 of the invention can include more than two chambers, wherein each individual chamber includes its own bag, gas generating cell, and activation circuit or mechanism. It is further understood that a single activation mechanism and/or electrochemical gas generating cell can be attached to and be responsible for generation of gas in more than one bag located in separate chambers. Likewise, each individual chamber can include a plurality of bags, gas generating cells, and activation mechanisms.

Delivery devices having multiple chambers facilitate the administration of different agents at specific times. For example, multiple antibiotic treatments can be administered in one self-contained unit, advantageously providing continuous or multiple dosages after insertion of the delivery device. In situations where cross-reactivity or stability between drugs is a concern, the multi-chambered delivery device 70 can provide a convenient means to admix a variety of incompatible drugs or agents within a single delivery device without compromising drug potency or purity.

FIG. 9 shows a top view of the multi-chambered delivery device 70 of FIG. 8. Construction line 66 illustrates the position of underlying chamber wall 66 in relation to the upper surface of first end 26. A plurality of outlet ports 68 are positioned on either side of the area occupied by chamber wall 66. Because the variations of shapes and configuration of outlet ports 68 that could be employed are innumerable, it is understood that the shapes and configurations shown in FIGS. 1 and 8 are merely exemplary. The shape and size of each individual outlet port and the placement of the outlet ports on the housing 22, first end 26, and second end 28 are only limited in that they should permit easy dispensation of the contents out of the delivery device 20.

FIGS. 10 and 11 illustrate a third embodiment of the delivery device in pre- and post-activation and administration phases. As depicted in FIG. 10, the delivery device includes a plunger 80 and a bag assembly which includes a bag 82, a gas generating cell 84 sealedly attached to the bag 82, and a activation switch 86 attached to the gas generating cell 84. The bag assembly of the present embodiment is functionally and structurally similar to the bag assemblies discussed thus far, except that the activation switch 86 is disposed on and lies substantially parallel to the interior surface 56 of second end 28 of the device. The gas generating cell 84 is attached to and disposed between gas generating cell 86 and the bag 82. The bag 82 also includes a coupling 88 to interconnect the bag 82 to the plunger 80. The coupling device can be made of any material that is compatible with the bag 82 and plunger 80.

The plunger 80 is made of rubber, plastic, metal, or any other suitable material which allows for a slidably tight fit within the interior surface 50 of the housing 22. The plunger 80 is preferably made of plastic when the beneficial agent to be administered is viscous and made of rubber when the beneficial agent being administered is thin and runny. The plunger is shaped to provide complementary engagement with interior surface 54 of first end 26 and includes two side surfaces 90 and a top surface 92. Side surfaces 90 are shaped to conform to and snugly fit within the interior surface 50 of the housing 22 so that the plunger is forced upwardly upon inflation of the bag 82, causing the contents of the housing 22 to be pushed out through outlet ports (not shown) on first end 26. The side surfaces 90 of plunger 80 include axially spaced apart seals 94 for making tight but slidable contact with the interior surface 50 of the housing 22. The plunger 80 is initially positioned in the housing 22 at a location to define a cavity or reservoir above the plunger 80, between interior surfaces 50 of housing 22, and below interior surface 54 of first end 26.

As shown in FIG. 10, the reservoir contains a first beneficial agent 96 and a second beneficial agent 98, which can be separated by a barrier 100 made of nonreactive material, such as Teflon (PTFE). The barrier 100 can be made of any material that is insoluble to and prevents passage of agents in contact the barrier 100 through the same. Although the instant delivery system contains two agents for delivery, it is understood that any number of agents can be included in the delivery device.

The anchoring mechanism includes a rigid section 102 and collapsible or retractable sections 104. The collapsible sections 104 are preferably bent or collapsed onto and in substantially parallel alignment with outer surfaces of the housing 22 by any suitable securing means, such as by securing a soluble band (shown here as dashed line 106) around the collapsible sections 104 and housing 22. Alternatively, the entire delivery device can be encapsulated with a relatively quickly soluble encapsulating material, such as gelatin, to temporarily secure the collapsible sections 104 of the anchoring device 24 to housing 22. Securing collapsible sections 104 in such manner facilitates insertion of the delivery device down the alimentary canal of the animal.

As illustrated in FIG. 11, once the delivery device reaches the first stomach of the ruminant animal, the soluble band or encapsulating material dissolves, and the collapsible sections 104 of the anchoring mechanism 24 are released. Upon release, the collapsible sections 104 extend out to a resting position which is in substantial perpendicular alignment with respect to housing 22, which prevents the delivery device from exiting the stomach area. Upon activation of the switch 86, gas generating cell 84 produces gas (or gases) that inflate bag 82 and force plunger 80 upwardly and into interior surface 54, thus forcing second agent 98 and first agent 96 out of housing 22 through the outlet port(s) (not shown).

FIGS. 12 through 15 illustrate a third embodiment of the delivery device 110 of the present invention. As shown in FIGS. 12 and 13, the delivery device 110 includes a housing 22 and an anchoring mechanism 24 attached to a first end 112 of the housing 22. The first end 112 of the housing 22 terminates with the outlet port 30. A second end 114 of the housing 22 includes an alignment slot 116 disposed on a housing collar 122 for receiving an alignment tab 118, located on a gas generating module 120, to facilitate alignment of the housing 22 and the gas generating module 120.

The gas generating module 120 further includes the gas generating cell 44, a activation switch (not shown), threads 124, and an activation button 128. A threaded nut 130 surrounds the housing 22 and is shaped to allow movement of the threaded nut 130 up and down the housing 22. The housing collar 122 can be shaped to prevent removal of the threaded nut 130 from around the housing 22. The threaded nut 130 includes threads 134 to receive the threads 124 of the gas generating module 120 and thereby fasten the gas generating module 120 to the housing 22. An O-ring 142, included on the gas generating module 120, forms a fluid seal between the gas generating module 120 and the housing 22.

Associated between the gas generating cell 44 and the housing 22 is a piston or plunger 140. The plunger 140 is flexible and has an interference fit with an interior surface 142 of the housing 22, which forms a gas seal between the plunger 140 and the beneficial agent contained within the housing 22. The plunger 140 can be made of any suitable material that is flexible and substantially fluid impermeable, such as an elastomer, a plastic, or a combination thereof.

Referring to FIGS. 14 and 15, the delivery device 110 is shown in pre-activation and activated stages. As shown in FIG. 14, prior to activation, the housing 22 of the delivery device 110 is filled with a beneficial agent 150 to be administered. The plunger 140 is then inserted into the housing 22 to the point where the plunger 140 makes contact with the beneficial agent 150. The gas generating module 120 is then inserted into the housing 22 by positioning the gas generating cell 44 against an inside surface 152 of the plunger 44. Once the gas generating cell 44 has been adequately associated with the plunger 44, the alignment tab 118 and the alignment slot 116 are aligned and joined. The threaded nut 130 is then positioned to contact the threads 124 of the gas generating module 120 and the threaded nut 130 is turned until the gas generating module 120 has been securely fastened to the housing 22. Alternatively, the gas generating module 120 can be attached to the housing 22 by any other suitable attaching means, such as, for example, an adhesive, a solvent, an ultrasonic weld joint, or a snap fit.

The gas generation cell 44 can be actuated by compressing the activation button 128. As previously described, activation can alternatively be preset by directly or indirectly activating or programming the activation mechanism (not shown), which, in turn, controls the gas generating cell 44. Upon activation of the gas generating cell 44, gas is generated which pressurizes a cavity formed between the gas generating cell 44 and the inside surface 152 of the plunger 140. As depicted in FIG. 15, this pressurization causes the plunger 140 to move toward the beneficial agent 150, which in turn displaces the beneficial agent 150 through the outlet port 30 and into the stomach or ruminal cavity of the animal.

Several of the devices shown in FIGS. 14 and 15 were fabricated and filled with either No. 2 grease. The devices were operated at a temperature of 38° C. FIG. 16 illustrates the performance characteristics, in terms of average volume dispensed over time, of such devices.

Although the invention has been described in detail with respect to specific delivery devices and methods of making and using the same, it should be realized that certain modifications can be made within the scope and spirit of the invention by those skilled in the art. For example, variations in the number of chambers contained within each enclosure, in the number and configuration of bag assemblies within each enclosure or chamber, and in the agents to be administered by the delivery device are contemplated.

What is claimed is:

1. A method of delivering a beneficial agent into a body cavity of a being comprising the steps of:

providing an apparatus including an enclosure having a volume and at least one chamber, each such chamber having a self-contained gas generating cell integrally associated therewith, said volume containing the beneficial agent, and an outlet port configured so as to permit passage of the beneficial agent from within the apparatus;

inserting the apparatus within a body cavity;

activating a gas generating cell and, in turn, generating a gas to create sufficient force against the beneficial agent; and controllably forcing the beneficial agent out of said enclosure via the outlet port in fluid communication with a body cavity, thus dispersing the beneficial agent into a body cavity.

2. The method of claim 1, wherein said gas is generated at a controlled rate to disperse the beneficial agent into the body cavity at a controlled rate.

3. The method of claim 2, wherein the beneficial agent is dispersed over a period of 1 to 700 days.

4. The method of claim 1, wherein said controlled displacing member comprises a fluid-tight bag.

5. The method according to claim 1 further comprising the step of:

deploying an anchoring member, to, in turn, preclude inadvertent removal of the apparatus from within a body cavity.

6. The method according to claim 5 wherein the step of deploying an anchoring member further comprises the step of deploying at least one collapsible section into a deployed position.

7. The method according to claim 6 wherein the step of deploying the at least one collapsible section further includes the step of temporarily precluding deployment of the at least one collapsible section until desired.

8. The method according to claim 7 wherein the step of temporarily precluding deployment comprises the steps of:

securing the at least one collapsible section with a soluble band; and dissolving the soluble band.

9. The method according to claim 1 wherein:

the apparatus includes at least two separate beneficial agents, and at least two self-contained gas generating cells, the step of activating further including the steps of:

activating the first self contained gas generating cell; and activating the second self contained gas generating cell, and the step of controllably forcing further including the steps of:

controllably forcing the first beneficial agent out of the opening of the apparatus by way of the gas generated by the first self-contained gas generating cell; and controllably forcing the second beneficial agent out of the opening of the apparatus by way of the gas generated by the second self-contained gas generating cell.

10. The method according to claim 9 wherein the step of first beneficial agent is delivered at higher rate than the second beneficial agent.

11. The method according to claim 1 wherein the apparatus includes two agents, the step of controllably forcing the at least one beneficial agent comprises the step of:

controllably forcing the first beneficial agent through the opening in the apparatus; and controllably forcing the second beneficial agent through the opening in the apparatus sequentially, after substantial depletion of the first beneficial agent.

12. The method according to claim 1 wherein the step of activating comprises the step of:

transmitting a signal to a receiver associated with the gas generating cell;

receiving the signal at the gas generating cell, to, in turn, activate the cell.

13. The method according to claim 1 wherein the step of activating comprises the step of:

setting a timer associated with the gas generating cell, wherein expiration of the timer activates the cell.

14. The method according to claim 1 wherein the apparatus includes a controlled displacing member associated with the chamber, the step of activating the gas generating cell, generates a gas to create sufficient force to move the controlled displacing member against the beneficial agent.

15. The method of claim 1, wherein said controlled displacing member comprises a piston.

* * * * *